United States Patent [19]
Hilvert et al.

[11] Patent Number: 5,843,414
[45] Date of Patent: Dec. 1, 1998

[54] ANTIPERSPIRANT CREAM COMPOSITIONS WITH IMPROVED DRY SKIN FEEL

[75] Inventors: Jennifer Elaine Hilvert, Cincinnati; Christine Marie Putman, West Chester; David Frederick Swaile, Cincinnati, all of Ohio

[73] Assignee: The Procter & Gamble Company, Cincinnati, Ohio

[21] Appl. No.: 856,771

[22] Filed: May 15, 1997

[51] Int. Cl.$^6$ ....................................................... A61K 7/32
[52] U.S. Cl. ............................ 424/65; 424/400; 424/401
[58] Field of Search ............................... 424/401, 65, 400

[56] References Cited

U.S. PATENT DOCUMENTS

| | | |
|---|---|---|
| 5,019,375 | 5/1991 | Tanner et al. . |
| 5,069,897 | 12/1991 | Orr . |
| 5,292,530 | 3/1994 | McCrea et al. . |
| 5,433,943 | 7/1995 | Osipow et al. . |

OTHER PUBLICATIONS

Gardner, Gardner's Chemical Synonyms and Trade Names (10th Edition), p. 836, 1994.

*Primary Examiner*—Thurman K. Page
*Assistant Examiner*—Brian K. Seidleck
*Attorney, Agent, or Firm*—William J. Winter; Tara M. Rosnell; David L. Suter

[57] ABSTRACT

Disclosed are antiperspirant cream compositions with improved dry skin feel. These antiperspirant compositions have a penetration force value of from about 20 gram·force to about 500 gram·force, and comprise (a) from about 20% to about 80% by weight of a volatile silicone material; (b) from about 5% to about 35% of a particulate antiperspirant active; (c) from about 0.1% to about 20% by weight of a gellant material comprising glyceryl tribehenate and other triglycerides wherein at least about 75% of the esterified fatty acid moieties of said other triglycerides have from about 18 to about 36 carbon atoms, and the molar ratio of glyceryl tribehenate to said other triglycerides is from about 20:1 to about 1:1; and (d) from about 0.1% to about 5% by weight of a drying agent selected from the group consisting of bentonite clays, hectonite clays, colloidal silicas, talc, microthene, and mixtures thereof. The compositions preferably further comprise a residue masking material.

20 Claims, No Drawings

ANTIPERSPIRANT CREAM COMPOSITIONS WITH IMPROVED DRY SKIN FEEL

TECHNICAL FIELD

The present invention relates to antiperspirant cream compositions with improved dry feel characteristics. In particular, the present invention relates to antiperspirant cream compositions comprising drying agents used in combination with volatile silicone emollients and select triglyceride gellants.

BACKGROUND OF THE INVENTION

There are many types of topical antiperspirant products that are commercially available or otherwise known in the antiperspirant art. Most of these products are formulated as sprays, roll-on liquids, creams, or solid sticks, and comprise an astringent material, e.g. zirconium or aluminum salt, incorporated into a suitable topical carrier. These products are designed to provide effective perspiration and odor control while also being cosmetically acceptable during and after application onto the axillary area or onto other areas of the skin. Aerosol sprays and solid sticks have been especially popular with consumers.

Although historically less preferred by consumers, antiperspirant creams remain an effective alternative to antiperspirant sprays and solid sticks. These creams can be applied by conventional means, or packaged into topical dispensers to make topical application more efficient and less messy. Perspiration and odor control provided by these products can be excellent. Many of these creams, however, are cosmetically unacceptable to a large number of antiperspirant users. Application of these creams can be messy, difficult to spread and wash off, and even when a cream applicator is employed, the applied areas often feel wet or sticky for several minutes after application. Many consumers have therefore preferred antiperspirant sticks for ease of administration and drier skin feel immediately after application, although the antiperspirant sticks typically leave an undesirably high residue on the skin.

It has been found that antiperspirant cream compositions which comprise a volatile silicone solvent, particulate antiperspirant actives and a select molar ratios of certain triglyceride gellants, provides effective antiperspirant and odor control, and improved cosmetics (reduced stickiness, improved ease of spreading, reduced dry-down times, improved wash-off, reduced grittiness) during and after application onto skin. The triglyceride gellant material described herein, when combined with volatile silicone solvents, provides a stable structure containing a dispersion of particulate antiperspirant actives, even when higher concentrations of volatile silicones are used.

It has now been found that low concentrations of materials such as bentonite clay, hectonite clay, colloidal silica, talc, and microthene can be used in the above-described antiperspirant cream compositions to provide a drier skin feel. These drying agents are especially effective when used in combination with the select triglyceride gellants and higher concentrations of the volatile silicones as described herein.

It is therefore an object of the present invention to provide an antiperspirant cream composition that remains stable over extended periods, contains higher concentrations of volatile silicone materials, has an improved dry skin feel, and provides effective antiperspirant and deodorant performance in cosmetically acceptable cream compositions.

SUMMARY OF THE INVENTION

The present invention is directed to antiperspirant compositions in a cream formulation which have a penetration force value of from about 20 gram·force to about 500 gram·force. These compositions comprise (a) from about 20% to about 80% by weight of a volatile silicone solvent; (b) from about 5% to about 35% by weight of a particulate antiperspirant active; (c) from about 0.1% to about 20% by weight of a gellant material comprising glyceryl tribehenate and other triglycerides wherein at least about 75% of the fatty acid esters moieties of said other triglycerides have from about 18 to about 36 carbon atoms, and the molar ratio of glyceryl tribehenate to said other triglycerides is from about 20:1 to about 1:1; and (d) from about 0.1% to about 5% by weight of a drying agent selected from the group consisting of bentonite clays, hectonite clays, colloidal silicas, talc, microthene, and mixtures thereof. The present invention is also directed to a method of treating and preventing perspiration in humans by using these compositions.

DETAILED DESCRIPTION OF THE INVENTION

The antiperspirant cream compositions of the present invention are liquid dispersions of particulate solids in a continuous water-insoluble or lipophilic phase. These cream compositions are suitable for use in roll-on or topical cream applicators, or by other conventional means of topical application, for depositing antiperspirant material onto human skin.

The antiperspirant cream compositions of the present invention have a penetration force value of from about 20 gram·force to about 500 gram·force, at 27° C., 15% relative humidity, as measured with a TA-XT2 Texture Analyzer, manufactured by Texture Technology Corp, Scarsdale, N.J., U.S.A. This value is the force required to move a standardized 45° cone through the product, for a distance of 10 mm, at a rate of 2 mm/second. The angled cone is also available from Texture Technology Corp., as part number TA-15, and has a total cone length of about 24.7 mm, an angled cone length about 18.3 mm, a maximum diameter of the angled surface of the cone of about 15.5 mm. The cone is a smooth, stainless steel construction and weighs about 17.8 grams. The antiperspirant cream composition of the present invention does not include solid antiperspirant stick compositions, which solid sticks have force penetration values substantially greater than about 500 gram·force, typically above about 1000 gram·force.

Preferred application of the antiperspirant compositions include roll-on application, and topical application using a cream applicator device. For roll-on application, the composition of the present invention has a penetration force value of from 20 gram·force to about 100 gram·force, preferably from about 35 gram·force to about 70 gram·force. For use as a conventional antiperspirant cream, or for use in a cream applicator device, the composition has a penetration force value of from about 100 gram·force of about 500 gram·force, preferably from about 120 gram·force to about 250 gram·force, more preferably from about 140 gram·force to about 200 gram·force.

The antiperspirant compositions of the present invention can comprise, consist of, or consist essentially of the essential elements and limitations of the invention described herein, as well as any of the additional ingredients, components, or limitations described herein.

As used herein, all parts, percentages and ratios are by weight of the total composition unless otherwise specified.

Volatile Silicone Solvent

The antiperspirant composition of the present invention comprises a volatile silicone solvent at concentrations ranging from about 20% to about 80%, preferably from about 30% to about 70%, more preferably from about 45% to about 70%, by weight of the composition. The volatile silicone solvent may be cyclic or linear.

"Volatile silicone" as used herein refers to those silicone materials which have measurable vapor pressure under ambient conditions. Nonlimiting examples of suitable volatile silicones are described in Todd et al., "Volatile Silicone Fluids for Cosmetics", Cosmetics and Toiletries, 91:27–32 (1976), which descriptions are incorporated herein by reference. Preferred volatile silicone materials are those having from about 3 to about 7, preferably from about 4 to about 5, silicon atoms.

Cyclic volatile silicones are preferred for use in the antiperspirant compositions herein, and include those represented by the formula:

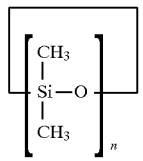

wherein n is from about 3 to about 7, preferably from about 4 to about 5, most preferably 5. These cyclic silicone materials will generally have viscosities of less than about 10 centistokes at 25° C.

Linear volatile silicone materials suitable for use in the antiperspirant compositions include those represented by the formula:

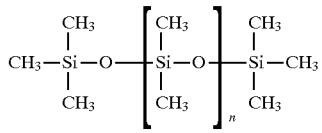

wherein n is from about 1 to about 7, preferably from about 2 to about 3. These linear silicone materials will generally have viscosities of less than about 5 centistokes at 25° C.

Specific examples of volatile silicone solvents suitable for use in the antiperspirant compositions include, but are not limited to, Cyclomethicone D-5 (commercially available from G. E. Silicones), Dow Corning 344, Dow Corning 345, and Dow Corning 200 0.5 csk (commercially available from Dow Corning Corp.), GE 7207 and 7158 (commercially available from General Electric Co.), and SWS-03314 (commercially available from SWS Silicones Corp.).

Particulate Antiperspirant Materials

The compositions of the present invention comprise particulate antiperspirant materials at concentrations ranging from about 5% to about 35%, preferably from about 10% to about 30%, antiperspirant active by weight of the compositions. These weight percentages are calculated on an anhydrous metal salt basis (exclusive of glycine, the salts of glycine, or other complexing agents). The particulate antiperspirant materials preferably have particle sizes ranging from about 1 to about 100 microns, more preferably from about 1 to about 50 microns. The particulate materials may be impalpable or microspherical in form.

Particulate antiperspirant materials suitable for use herein are those which comprise any compound, composition or mixture thereof having antiperspirant activity. Astringent metallic salts are preferred antiperspirant materials for use herein, particularly the inorganic and organic salts of aluminum, zirconium and zinc, as well as mixtures thereof. Particularly preferred are the aluminum and zirconium salts, such as aluminum halides, aluminum hydroxy halides, zirconyl oxide halides, zirconyl hydroxy halides, and mixtures thereof.

Preferred aluminum salts are those represented by the formula:

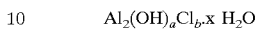

wherein a is from about 2 to about 5; the sum of a and b is about 6; x is from about 1 to about 6; and wherein a, b, and x may have non-integer values. Particularly preferred are the aluminum chlorhydroxides referred to as "5/6 basic chlorhydroxide", wherein a=5, and "2/3 basic chlorhydroxide", wherein a=4. Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, Gosling et al., issued Nov. 16, 1982; and British Patent Specification 2,048,229, Fitzgerald et al., published Dec. 10, 1980, all of which are incorporated herein by reference. Mixtures of aluminum salts are described in British Patent Specification 1,347,950, Shin et al., published Feb. 27, 1974, also incorporated herein by reference.

Zirconium salts are also preferred for use in the antiperspirant compositions. These salts are represented by the formula:

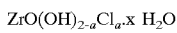

wherein a is from about 1.5 to about 1.87; x is from about 1 to about 7; and wherein a and x may have non-integer values. These zirconium salts are described in Belgian Patent 825,146, Schmitz, issued Aug. 4, 1975, incorporated by reference herein. Particularly preferred zirconium salts are those complexes which additionally contain aluminum and glycine, commonly known as ZAG complexes. Such ZAG complexes contain aluminum chlorhydroxide and zirconyl hydroxy chloride of the formulae described above. Such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. No. 4,120,948, Shelton, issued Oct. 17, 1978, all of which are incorporated by reference herein.

Triglyceride Gellant

The antiperspirant composition of the present invention comprises a gellant material comprising a select molar ratio of certain specified triglycerides. The gellant material, when combined with the volatile silicone solvent described hereinbefore, provides the composition with a physically stable structure within which the particulate antiperspirant materials are dispersed, and maintained as such over an extended period of time.

The antiperspirant composition comprises from about 0.1% to about 20%, by weight of the gellant material, wherein the gellant material comprises glyceryl tribehenate and other triglycerides, wherein at least about 75%, preferably about 100%, of the esterified fatty acid moieties of said other triglycerides each have from about 18 to about 36 carbon atoms, and wherein the molar ratio of glyceryl tribehenate to said other triglycerides is from about 20:1 to about 1:1, preferably from about 10:1 to about 3:1, more preferably from about 6:1 to about 4:1. The esterified fatty acid moieties may be saturated or unsaturated, substituted or unsubstituted, linear or branched, but are preferably linear, saturated, unsubstituted ester moieties derived from fatty acid materials having from about 18 to about 36 carbon atoms. The triglyceride gellant material preferably has a melting point of less than about 110° C., more preferably between about 60° C. and 110° C.

It has been found that this triglyceride-based gellant material, when combined with volatile silicone solvents, and when used in the above-described molar ratio, provides a stable structure for maintaining a dispersion of particulate antiperspirant material in a topical formulation. This triglyceride gellant is especially useful in maintaining the physical stability of particulate dispersions containing higher concentrations of volatile silicone solvents.

It has also been found that penetration force values for the antiperspirant compositions can be controlled by adjusting total triglyceride concentrations while maintaining the above-described molar ratios. In controlling penetration force values in this manner, there is no longer a need to use organic solvents to control penetration force values, which solvents often add cost to the formulation, introduce additional compatibility issues, and often contribute undesirable cosmetics such as prolonged stickiness, increased dry-down times, and reduced dry feel after application.

Preferred concentrations of the gellant material ranges from about 0.5% to about 15% by weight of the composition. Specific concentrations are selected depending on the desired penetration force value. For roll-on formulations having a penetration force value of from about 20 gram·force to about 100 gram·force, triglyceride concentrations preferably range from about 1% to about 5% by weight of the antiperspirant composition. For other cream formulations, including those formulations suitable for use in cream applicator devices, which have a penetration force value of from about 100 gram·force to about 500 gram·force, triglyceride concentrations preferably range from about 4% to about 20%, preferably from about 4% to about 10%, by weight of the antiperspirant composition.

A particularly preferred embodiment of the present invention are antiperspirant cream compositions described herein which are packaged in suitable cream applicator devices. Nonlimiting examples of suitable cream applicator devices include those described in U.S. Pat. No. 5,000,356, which description is incorporated herein by reference.

Specific examples of triglyceride gellants for use in the antiperspirant compositions that are commercially available include, but are not limited to, tristearin, hydrogenated vegetable oil, rape seed oil, castor wax, fish oils, tripalmiten, Syncrowax® HRC and Syncrowax® HGL-C (Syncrowax® available from Croda, Inc.).

Drying Agent

The antiperspirant composition of the present invention comprises a drying agent to provide improved dry skin feel. Concentrations of the drying agent range from about 0.1% to about 5%, more preferably from about 0.3% to about 3%, even more preferably from about 0.5% to about 2%, by weight of the composition.

Suitable drying agents are typically in the form of inert solid particulates, and include materials such as talc, microthene, silicates, colloidal silicas, and mixtures thereof. These materials provide benefits such as dry feel and aesthetics, especially dry feel benefits.

Silicates suitable for use in the antiperspirant composition include montmorillonite clays and hydrophobically treated montmorillonites, examples of which include bentonites, hectonites, colloidal magnesium silicates, and mixtures thereof. Commercially available silicates include the Bentone series of hydrophobic bentonites available from NL Industries, Inc.

Preferred drying agents for use herein include fumed silicas, especially finely divided fumed silicas or colloidal silicas. Fumed silicas are typically in the form of fluffy, white powders which comprise micron to sub-micron sized silica particulates having relatively high surface areas of from about 2.5 m$^2$/gm to about 1,200 m$^2$/gm. Preferred fumed silicas are those having an average particle diameter of less than about 1.0 μm, and a surface area of from about 100 m$^2$/gm to about 1,200 m$^2$/gm. Fumed silicas are a form of colloidal silicas which are typically made by hydrolyzing silicon tetrachloride at high temperatures to form fumed silicas which contain about 99.8% by weight (on a moisture free basis) of silicon dioxide. Colloidal silica materials are well known in the art, and are described in Hardy, et al. "The Use of Fumed Silica in Cosmetics", 2 *Cosmetic Technology* 35 (1980), and R. Iler, *The Chemistry of Silica* (1979), which descriptions are incorporated herein by reference.

Colloidal silica materials suitable for use herein are available from a variety of sources, including Syloid silicas (manufactured by Davison Chemical Division of W. R. Grace), Cab-O-Sil (manufactured by Cabot Corporation), and Aerosil (manufactured by Degussa A.G.). Cab-O-Sil is a preferred commercially available colloidal silica useful herein, with a surface area ranging from about 200 m$^2$/gm to about 400 m$^2$/gm.

Optional Residue Masking Material

The antiperspirant composition of the present invention may further comprise a nonvolatile emollient as a residue masking material. Such materials and their use in antiperspirant products are well known in the antiperspirant art, and any such material may be incorporated into the composition of the present invention, provided that such optional material is compatible with the essential elements of the composition, or does not unduly impair product performance or cosmetics.

Concentrations of the optional residue masking material ranges from about 0.1% to about 40%, preferably from about 1% to about 10%, by weight of the antiperspirant composition. These optional materials are liquid at ambient temperatures, and are nonvolatile. The term "nonvolatile" as used in this context refers to materials which have a boiling point under atmospheric pressure of at least about 200° C. Nonlimiting examples of suitable residue masking materials for use in the antiperspirant products include butyl stearate, diisopropyl adipate, petrolatum, nonvolatile silicones, octyldodecanol, phenyl trimethicone, isopropyl myristate, C12–15 ethanol benzoate, mineral oil, and PPG-14 Butyl Ether. Residue masking materials are described, for example, in U.S. Pat. No. 4,985,238, which description are incorporated herein by reference. Nonvolatile silicones such as Dow Corning 200 10 csk and Dow Corning 200 20 csk (available from Dow Corning Corp.) are the preferred optional residue masking materials.

Optional Materials

The antiperspirant compositions of the present invention may further comprise one or more other optional materials which modify the physical characteristics of the compositions or serve as additional "active" components when deposited on the skin. Many such optional materials are known in the antiperspirant art and may be used in the antiperspirant compositions herein, provided that such optional materials are compatible with the essential materials described herein, or do not otherwise unduly impair product performance.

Nonlimiting examples of optional materials include active components such as bacteriostats and fungiostats, and "nonactive" components such as colorants, perfumes, emulsifiers, chelants, distributing agents, preservatives, and wash-off aids. Examples of such optional materials are described in U.S. Pat. No. 4,049,792, Elsnau, issued Sep. 20, 1977; Canadian Patent 1,164,347, Beckmeyer et al., issued Mar. 27, 1984; U.S. Pat. No. 5,019,375, Tanner et al., issued May 28, 1991; and U.S. Pat. No. 5,429,816, Hofrichter et al., issued Jul. 4, 1995; which descriptions are incorporated herein by reference.

Method of Manufacture and Use

Methods for making the compositions of the present invention, as well as the equipment used in such methods, are well known to those skilled in the art. They may be batch processes involving discrete processing steps or involving continuous processes wherein the product composition is passed between processing steps in essentially continuous increments. The process may be as simple as thoroughly mixing together all of the components at the desired temperature, typically from about −35° C. to about 100° C., and then allowing the heated mixture to cool to room temperature. Specific essential and non-essential materials, at specific concentrations, are selected to produce a cream of desired aesthetics and viscosity, which deposits a suitable amount of antiperspirant active on the skin during use. In making the compositions of the present invention care must be taken to assure that the particulate antiperspirant materials are dispersed relatively uniformly throughout the composition.

The antiperspirant cream compositions of the present invention may be packaged in conventional antiperspirant cream containers known in the art. Such packages typically contain the cream in bulk form. The cream is then applied by hand, or by a pad or similar applicator device. These creams may also be packed in a dispenser designed to extrude or otherwise directly apply the creams to the skin. The cream compositions of the present invention may by packaged in known or conventional roll-on applicators, and applied to the skin by application of the roll-on device to the skin.

The antiperspirant compositions of the present invention are utilized in a conventional manner to treat or prevent perspiration on areas of the human body, such as the axillary areas, which are prone to perspiration wetness. Specifically, an effective amount of any of the compositions described herein is applied topically to such areas one or more times a day. When this is done, the compositions provide effective antiperspirant performance, as well as reduced residue on the skin, and good aesthetics upon application for the user.

EXAMPLES

The following nonlimiting examples illustrate specific embodiments of the antiperspirant compositions of the present invention, including methods of manufacture and use.

Example I

The following describes an antiperspirant composition of the present invention. All of the listed components are combined and heated to 100° C. with agitation, and cooled to 52° C. The composition is then filled into jars or cream applicators and allowed to cool and form a stiff cream. The penetration force value of the resulting composition is about 225 gram·force.

| Component | Weight % |
| --- | --- |
| Cyclomethicone D5[1] | 62.0 |
| Aluminum zirconium trichlorohydrex gly[2] | 25.25 |
| Dimethicone 10 csk[3] | 5.0 |
| Glyceryl tribehenate | 5.0 |
| C18–C36 triglyceride combination[4] | 1.25 |
| Cab-O-Sil[5] | 1.0 |
| Perfume | 0.5 |

[1] A cyclic polydimethylsiloxane containing 5 carbons, supplied by G. E. Silicones
[2] Supplied by Westwood Chemical Corporation
[3] A nonvolatile silicone supplied by Dow Corning
[4] Syncrowax HGL-C, supplied by Croda, Inc.
[5] Supplied by Cabot Corporation

Example II

The following describes an antiperspirant composition of the present invention. All of the listed components are combined and heated to 100° C. with agitation, and cooled to about 52° C. The composition is then filled into jars or cream applicators and allowed to cool and form a stiff cream. The penetration force value of the resulting composition is about 225 gram·force.

| Component | Weight % |
| --- | --- |
| Cyclomethicone D5[1] | 62.70 |
| Aluminum zirconium trichlorohydrex gly[2] | 26.0 |
| Dimethicone 10 csk[3] | 5.0 |
| Glyceryl tribehenate | 3.25 |
| C18–C36 triglyceride combination[4] | 0.80 |
| Cab-O-Sil[5] | 1.75 |
| Perfume | 0.5 |

Example III

The following describes an antiperspirant composition of the present invention. The listed components are combined and heated to 100° C. with agitation, and cooled to 52° C. The composition is then packaged in jars or cream applicators and allowed to cool. The penetration force value of the resulting composition is about 185 gram·force.

| Component | Weight % |
| --- | --- |
| Cyclomethicone D5[1] | 60.5 |
| Aluminum zirconium trichlorohydrex gly[2] | 26.0 |
| Dimethicone 10 csk[3] | 5.0 |
| Glyercyl tribehenate | 5.0 |
| C18–C36 triglyceride combination[4] | 1.25 |
| Talc | 1.75 |
| Perfume | 0.5 |

Example IV

The following describes an antiperspirant composition of the present invention. The listed components are combined and heated to 100° C. with agitation, and cooled to 52° C. The composition is then packaged in jars or cream applicators and allowed to cool. The penetration force value of the resulting composition is about 185 gram·force.

| Component | Weight % |
| --- | --- |
| Cyclomethicone D5[1] | 62.25 |
| Aluminum zirconium trichlorohydrex gly[2] | 26.0 |
| Glyercyl tribehenate | 5.0 |
| C18–C36 triglyceride combination[4] | 1.25 |
| Talc | 5.0 |
| Perfume | 0.5 |

The antiperspirant compositions described in Examples I–IV, when applied to the axillary area of the user, provide effective prevention and control of perspiration wetness. These compositions remain physically stable over extended periods. These compositions also have reduced dry-down times, smoother and drier feel immediately after application, and reduced apparent residue.

What is claimed is:

1. An antiperspirant cream composition comprising:
   (a) from about 20% to about 80% by weight of a volatile silicone material;
   (b) from about 5% to about 35% by weight of a particulate antiperspirant active;
   (c) from about 0.1% to about 20% by weight of a gellant material comprising glyceryl tribehenate and other triglycerides wherein at least about 75% of the fatty acid esters moieties of said other triglycerides have from about 18 to about 36 carbon atoms, and the molar ratio of glyceryl tribehenate to said other triglycerides is from about 20:1 to about 1:1; and
   (d) from about 0.1% to about 5% by weight of a drying agent selected from the group consisting of bentonite clays, hectonite clays, colloidal silicas, talc, microthene, and mixtures thereof; and
   wherein the antiperspirant cream composition has a penetration force value of from about 20 gram·force to about 500 gram·force.

2. The composition of claim 1 wherein the composition comprises from about 0.5% to about 2% by weight of the drying agent.

3. The composition of claim 2 wherein the penetration force value is from about 20 gram·force to about 100 gram·force.

4. The composition of 2 wherein about 100% of the fatty acid esters moieties of said other triglycerides each comprise a linear, saturated, unsubstituted carbon chain having from about 18 to about 36 carbon atoms.

5. The composition of claim 2 wherein the volatile silicone material is a cyclic silicone represented by the formula

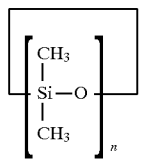

wherein n is from about 3 to about 7.

6. The composition of claim 2 wherein the colloidal silica is a fumed silica having a surface area of from about 200 $m^2$/gm to about 400 $m^2$/gm.

7. The composition of claim 2 further comprising from about 0.1% to about 40% by weight of a residue masking material.

8. The composition of claim 2 wherein the penetration force value is from about 100 gram·force to about 500 gram·force.

9. The composition of claim 8 wherein the molar ratio is from about 3:1 to about 10:1.

10. The composition of claim 8 wherein about 100% of the fatty acid esters moieties of said other triglycerides each comprise a linear, saturated, unsubstituted carbon chain having from about 18 to about 36 carbon atoms.

11. The composition of claim 8 wherein the volatile silicone material is a cyclic silicone represented by the formula

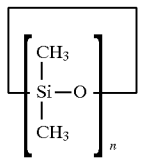

wherein n is from about 3 to about 7.

12. The composition of claim 8 wherein the colloidal silica is a fumed silica having a surface area of from about 200 $m^2$/gm to about 400 $m^2$/gm.

13. The composition of claim 8 further comprising from about 0.1% to about 40% by weight of a residue masking material.

14. An antiperspirant cream composition comprising:
   (a) from about 20% to about 80% by weight of a volatile cyclic silicone material;
   (b) from about 5% to about 35% by weight of a particulate antiperspirant active;
   (c) from about 0.1% to about 20% by weight of a gellant material comprising glyceryl tribehenate and other triglycerides wherein at least about 75% of the fatty acid esters moieties of said other triglycerides have from about 18 to about 36 carbon atoms, and the molar ratio of glyceryl tribehenate to said other triglycerides is from about 4:1 to about 6:1;
   (d) from about 0.1% to about 5% by weight of a drying agent selected from the group consisting of bentonite clays, hectonite clays, colloidal silicas, talc, microthene, and mixtures thereof; and
   (e) from about 0.1% to about 40% by weight of a residue masking material; and
   wherein the antiperspirant cream composition has a penetration force value of from about 20 gram·force to about 500 gram·force.

15. The composition of claim 14 wherein the composition comprises from about 0.5% to about 2% by weight of the drying agent.

16. The composition of claim 15 wherein the colloidal silica is a fumed silica having a surface area of from about 200 $m^2$/gm to about 400 $m^2$/gm.

17. The composition of claim 15 wherein the residue masking material is a nonvolatile silicone.

18. A method for treating and controlling perspiration in humans comprising the topical application to the axillary area of an effective amount of the antiperspirant composition of claim 3.

19. A method for treating and controlling perspiration in humans comprising the topical application to the axillary area of an effective amount of the antiperspirant composition of claim 8.

20. A method for treating and controlling perspiration in humans comprising the topical application to the axillary area of an effective amount of the antiperspirant composition of claim 14.

* * * * *